United States Patent
Treu (10) Patent No.: US 11,918,720 B2
(45) Date of Patent: Mar. 5, 2024

(54) MULTIPLE MODE TREATMENT DEVICES METHODS AND SYSTEMS

(71) Applicant: NxStage Medical, Inc., Lawrence, MA (US)

(72) Inventor: Dennis M. Treu, Castle Rock, CO (US)

(73) Assignee: NxStage Medical, Inc., Lawrence, MA (US)

(*) Notice: Subject to any disclaimer, the term of this patent is extended or adjusted under 35 U.S.C. 154(b) by 1081 days.

(21) Appl. No.: 16/483,203

(22) PCT Filed: Feb. 5, 2018

(86) PCT No.: PCT/US2018/016918
§ 371 (c)(1),
(2) Date: Aug. 2, 2019

(87) PCT Pub. No.: WO2018/145035
PCT Pub. Date: Aug. 9, 2018

(65) Prior Publication Data
US 2020/0230309 A1    Jul. 23, 2020

Related U.S. Application Data (60) Provisional application No. 62/454,394, filed on Feb. 3, 2017.

(51) Int. Cl.
*A61M 1/26* (2006.01)
*A61M 1/16* (2006.01)
(Continued)

(52) U.S. Cl.
CPC .......... *A61M 1/267* (2014.02); *A61M 1/1656* (2013.01); *A61M 1/1698* (2013.01);
(Continued)

(58) Field of Classification Search
None
See application file for complete search history.

(56) References Cited

U.S. PATENT DOCUMENTS 5,368,555 A   11/1994   Sussman et al.
6,472,200 B1  10/2002   Mitrani
(Continued)

FOREIGN PATENT DOCUMENTS

CN    202270211 U    6/2012
WO    2016057982 A1  4/2016
(Continued)

OTHER PUBLICATIONS

International Search Report and Written Opinion for International Application No. PCT/US2018/016918 dated Apr. 12, 2018.
(Continued)

*Primary Examiner* — Jonathan M Peo
(74) *Attorney, Agent, or Firm* — Potomac Law Group, PLLC (57) ABSTRACT

A blood treatment system employing at least two pumps for performing a low blood flow treatment is operable for high blood flow treatments such as extracorporeal membrane oxygenation (ECMO) by providing a fluid circuit with parallel blood flow paths and recruiting multiple ones of the pumps for parallel blood flow.

10 Claims, 5 Drawing Sheets

(51) Int. Cl.
*A61M 1/34* (2006.01)
*A61M 1/36* (2006.01)
*A61M 39/10* (2006.01)

(52) U.S. Cl.
CPC ........ *A61M 1/3455* (2013.01); *A61M 1/3623* (2022.05); *A61M 1/3639* (2013.01); *A61M 1/3672* (2013.01); *A61M 39/105* (2013.01); *A61M 2205/3334* (2013.01); *A61M 2205/3368* (2013.01); *A61M 2205/36* (2013.01); *A61M 2205/52* (2013.01)

(56) References Cited

U.S. PATENT DOCUMENTS

| | | |
|---|---|---|
| 8,979,788 B2 | 3/2015 | Demers et al. |
| 2007/0160495 A1 | 7/2007 | Schreyer |
| 2009/0060890 A1* | 3/2009 | Humes .................. A61P 37/02 |
| | | 435/308.1 |
| 2012/0130298 A1* | 5/2012 | Demers .................. G01F 22/02 |
| | | 137/565.17 |
| 2013/0284648 A1 | 10/2013 | Grant et al. |
| 2014/0174542 A1 | 6/2014 | Jansson et al. |
| 2014/0175010 A1 | 6/2014 | Rambod et al. |

FOREIGN PATENT DOCUMENTS

| | | |
|---|---|---|
| WO | 2016103290 A1 | 6/2016 |
| WO | 2018211434 A1 | 11/2018 |

OTHER PUBLICATIONS

Extended European Search Report dated Oct. 12, 2020 for European Patent Application No. 18748603.0.

* cited by examiner

Fluid treatment

Fluid and oxygenation treatments combined

MULTIPLE MODE TREATMENT DEVICES METHODS AND SYSTEMS

CROSS-REFERENCE TO RELATED APPLICATIONS

This application is a U.S. national stage filing under 35 U.S.C. § 371 of International Application No. PCT/US2018/016918 filed Feb. 5, 2018 (published as WO 2018145035 on Aug. 9, 2018), which claims the benefit of U.S. Provisional Application No. 62/454,394 filed Feb. 3, 2017, all of which are hereby incorporated by reference in their entireties.

BACKGROUND

Extracorporeal membrane oxygenation (ECMO), or extracorporeal life support (ECLS), is an extracorporeal treatment modality that provides cardiac and respiratory support to for patients with cardiac and/or pulmonary insufficiency. The treatment provides this by assisting with gas exchange with the blood in an extracorporeal blood circuit. In ECMO, blood extracted in a blood circuit and passed through a gas exchange cartridge or blood oxygenator. The blood circuit may be a non-bypass type system or a cardio-pulmonary bypass type system, the latter generally being used for short intervals.

Another class of treatment modalities is extra corporeal blood treatment performed by (ECBT systems), including hemodialysis, hemofiltration, hemodiafiltration, apheresis systems, etc. Such systems provide the maintenance of the overall fluid balance between the fluid added to the patient and the fluid withdrawn from the patient. Ideally, this exchange will result in a net loss or gain of fluid to/from the patient that precisely matches the patient's treatment requirement. To achieve this, the ECBT may employ a volumetric fluid balancing system, of which a variety of different types are known. For example, see U.S. Pat. Nos. 5,836,908, 4,728,433, 5,344,568, 4,894,150, and 6,284,131, each of which is hereby incorporated by reference as if fully set forth in their entireties herein.

Fluid balancing mechanisms generally attempt to ensure that the total mass or volume of fluid pumped into, and removed from, the non-blood side of a filter or dialysis are equal. To provide for a desired differential between the net quantity removed/added, the inflow and outflow rates can be controlled to produce a net difference. This may be provided by regulating the relative flow rates provided by ingoing and outgoing pumps or by using a separate bypass, driven by a separate pump. In an example, such a bypass pump pumps at an ultrafiltration ("UF") line rate which is added to the balanced withdrawal rate.

Gravimetric systems that balance flow by weighing mass from a source and collected fluid from the treatment device and comparing the two are known. Another approach is to measure incremental volume transfer. Hard plumbed or disposable lined balance chambers alternately fill and empty in a manner that assures equal and opposite volume exchange. Systems using this approach are balancing a single inlet fluid flow with an effluent stream. A second stream of fluid is frequently added to the extracorporeal circuit using an additional pump, or external IV pump. The volume of this second stream may be balanced by the isolated ultrafiltration (UF) pump to maintain patient fluid balance. This approach is limited by the calibration inaccuracies of the additional or external pump and the isolated UF pump. These inaccuracies are acceptable at low flow rates. However, at higher flow rates the cumulative volumetric inaccuracies may not achieve the desired patient volumetric balance. Additionally, this approach requires an operator to independently set the pump rates to achieve the desired balance.

Another function provided by extracorporeal blood treatment systems is the maintenance of blood temperature of the patient under treatment. Such extracorporeal blood treatments fall into a variety of categories ranging from blood oxygenation and therapeutic hypothermia to renal replacement therapies such as hemodialysis (HD). In extracorporeal blood treatments, such as HD, blood is pumped from a patient through a blood circuit and through a treatment device, such as a dialyzer. Toxins and electrolyte exchange across a dialyzer membrane to exchange with a treatment fluid. The exchange causes the removal of waste products in the blood and excess water. A substantial volume of the patient's blood may pass through an extracorporeal blood treatment system during the course of a treatment such that any heat transfer to or from the blood can upset the patient's body temperature.

ECBT may involve the use of multiple treatment fluid streams including multiple replacement fluids plus the delivery of citrate. Examples providing 4 pumps have been described, for example in US Patent Publication US20120150090 to Szamosfalvi, et al. The latter shows a blood pump, a citrate pump, and pumps for pre-dilution and post-dilution replacement fluid for implementation of a hemofiltration treatment.

Compared to the other ECBT treatments, ECMO requires a substantially higher blood flow rate. ECMO is ideally performed at blood flow rates requires flow rates of at least 1 to 3 L/min and can be performed at rates up to 9 L/min.

SUMMARY

The disclosed subject matter includes extracorporeal blood treatment devices, methods, and systems capable of providing ECBT treatments and ECMO treatments employing the same permanent system merely by employing respective disposable components. In embodiments of the disclosed subject matter, this is accomplished employing a system that has multiple non-blood pumps, for example, citrate and replacement fluid pumps for ECBT treatments and using the non-blood pumps in parallel for high volume blood flow for ECMO. In this way the plurality of non-blood pumps can achieve a higher flow volume than the single blood pump used in ECBT mode. The permanent system components provide a controller that runs the pumps at a suitable rate and direction to provide parallel flow from the patient, through the pumps, which are then recombined to flow through a blood oxygenator and back to the patient. In other embodiments, the blood may flow through multiple, potentially smaller, oxygenators for parallel treatment at higher flow rates. The control may be configured such that during ECMO, they run at higher speeds (e.g., peristaltic pump shaft speeds) as well as providing parallel flow of blood, thereby providing net blood volume rates suitable for ECMO.

In ECBT modes, volumetric fluid balancing may be performed for a single therapy fluid stream using a system configuration including balance chambers, peristaltic pumps, and mechanically controlled pinch valves. The therapy fluid entering the blood path of the extracorporeal circuit may be balanced with effluent removed from the blood path through the dialyzer of the circuit so that the patient volume is not affected by this exchange of fluids. The limitation to a single therapy fluid inlet flow is a common limitation of various dialysis machines that use balance chambers. Some extracorporeal therapies can use more than one therapy fluid inlet flow that may be volumetrically controlled to achieve an overall patient fluid balance. For example, the difference between the total fluid that moves into the patient (for example, by flowing into the patient's blood stream) and that withdrawn from the patient must be precisely controlled. For example, in dialysis treatment, the amount of fluid entering the patient, for example through predilution, post-dilution, citrate infusion, and reverse ultrafiltration streams may be balanced against the net ultrafiltration stream to achieve a target net ultrafiltration rate. The subject matter described in this disclosure provides machine configurations that support one or more therapy fluid flows synchronized with the effluent fluid flow from the extracorporeal circuit to achieve accurate fluid balance and the warming of fluid in such systems.

The disclosed subject matter includes several different system configurations that support ECMO and ECBT with one or more therapy fluid inlet flows balanced with the effluent flow. In ECBT, reliable flow balance may be obtained by synchronizing the pump flows by various control mechanisms. The temperature of the blood may be maintained by adding heat to a subset of the treatment fluid streams such that heat is transferred to the blood without creating a local temperature rise that might adversely affect the blood and so as to warm blood to a predefined temperature of the blood returned to the patient. To this end, the temperature of blood in a venous line (venous temperature) connected for return flow of blood to the patient is continuously monitored and used for negative feedback control. The set point of the return blood temperature can be established based on an estimate of the heat transfer from/to the environment between the point of the venous temperature measurement and the patient blood access (e.g., fistula needle, central line, or dual needle access).

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIG. 3A shows the configuration for pure fluid treatment.

DETAILED DESCRIPTION

Figure 1:
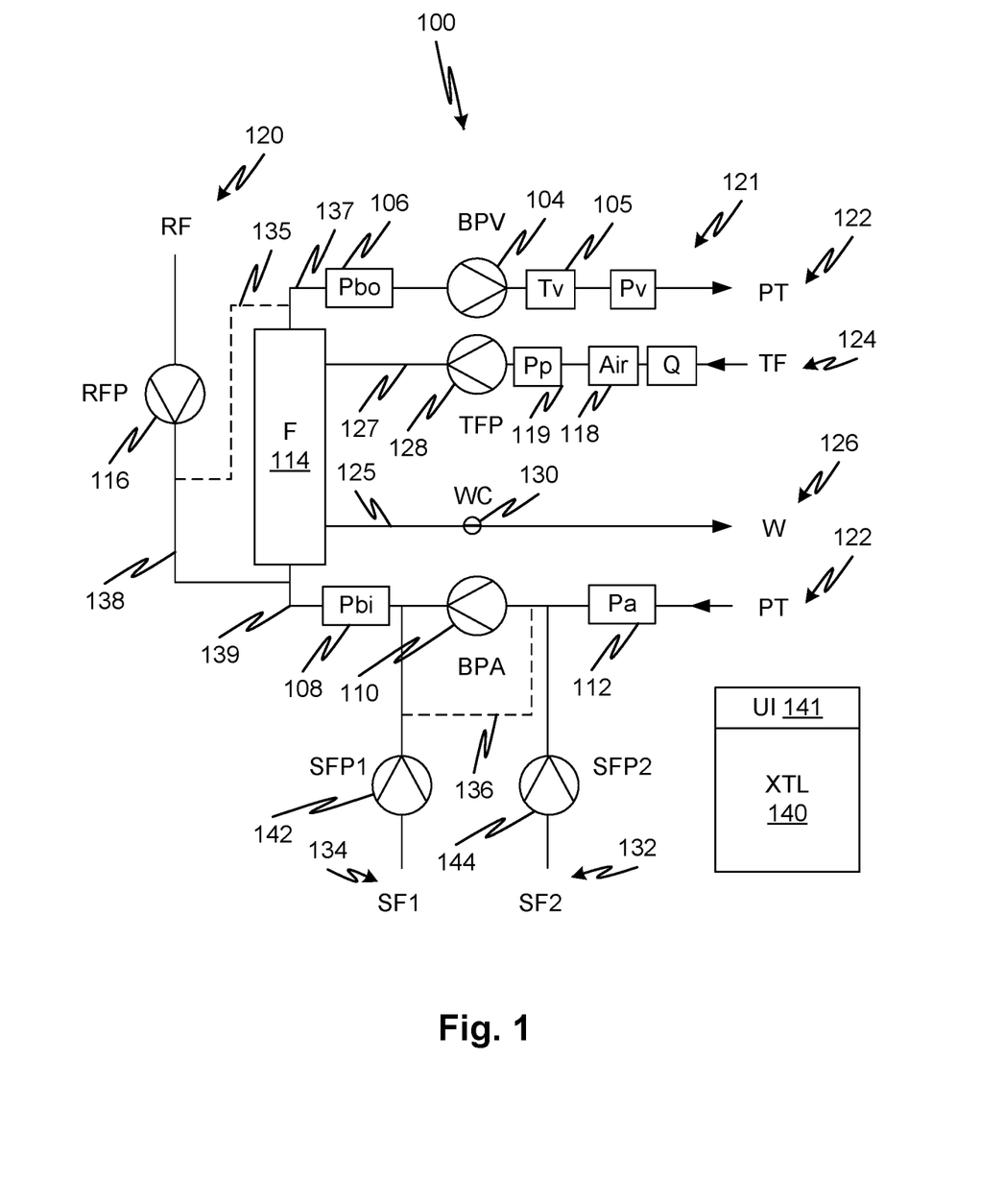
FIG. 1 shows a treatment fluid multi-stream blood treatment system that regulates the flow of blood relative to a treatment fluid to generate a cumulative target ratio of fluid drawn or infused into a patient over the course of a treatment while maintaining a blood temperature.

FIG. 1 shows a blood treatment system 100 that regulates the flow of fluid in a fluid circuit 121 that includes an arterial blood line 139, a venous blood line 137, a fresh treatment fluid line 127 and a waste treatment fluid line 125. In particular, the blood treatment system 100 regulates the flow of blood relative to a treatment fluid to generate a cumulative target ratio of fluid drawn or infused into a patient over the course of a treatment or drawn or returned to a priming fluid source/sink, respectively. The net flow of fluid into or out of a patient (priming fluid source/sink—hereafter any reference to "patient" and/or "blood" with reference to a synchronization mode or synchronization operation may be replaced by priming fluid and/or a combination source and sink thereof, because the synchronization mode/operation mode discussed herein can be done during priming with a recirculating or single-pass priming operation as well as during a treatment, as will be evident to the skilled artisan), at any given time, is determined by a then-instant difference between the volume of blood pumped from a treatment device 114 (labeled F for filter, for example a dialyzer, a common embodiment) to the volume pumped into the treatment device 114. Blood is pumped into the treatment device 114 by an arterial blood pump 110 and pumped from the treatment device 114 by a venous blood pump 104. The illustrated configuration is common for dialysis systems, and may include all the typical incidents thereof, but differs specifically in that there are two blood pumps: the arterial blood pump 110 and the venous blood pump 104.

During a treatment mode and also in embodiments of a synchronization mode, blood is pumped to a patient access 122 (venous access) and from a patient access 123 (arterial access). In other embodiments synchronization may be done instead with a priming fluid. During priming operations, the patient access or priming connector(s) may be connected to priming fluid source, sink, or recirculating container instead. Thus, 122/123 may be considered generally to represent a patient access connected to a patient, in which case the circulating fluid is blood, or 122/123 may be considered to represent a priming fluid source, sink, or recirculating container, in which case, the circulating fluid is priming fluid.

Control and sensing are provided by a controller 140 which may be of any form but typically some type of programmable digital controller, for example, an embedded computer including a user interface (UI) 141. A treatment fluid is pumped from a treatment fluid source 124 through an air detector 118, through the treatment device 114, past a waste line clamp 130, to the drain 126 (indicated by W for waste). Drain 126 may be a drain of a plumbing system or a collection container or any other device for disposal of waste treatment fluid. Treatment fluid 124 may be dialysate, replacement fluid, or any other medicament.

A replacement fluid 120 may be pumped into the arterial blood line 139 or the venous blood line 137 through a replacement fluid line 135 or 138, respectively (or both) for predilution, post-dilution or a combination of both. In alternative embodiments, the dilution may occur at a midpoint of the treatment device 114, for example by using two smaller units of a treatment device 114 that provides a junction between them or by means of a special structure of the treatment device 114 that provides for mid-dilution. The treatment device 114 may be adapted for a variety of types of blood treatment that require balancing flows into and out of a fluid circuit, including, but not limited to, dialysis, hemofiltration, hemodiafiltration, apheresis, adsorption, or hemoperfusion. These treatment modalities apply to all of the disclosed embodiments including those originally disclosed in the claims. Further supplemental fluids indicated by supplemental fluid 134 and supplemental fluid 132 may be pumped into the arterial blood line 139 by respective pumps, namely, supplemental fluid pump 142 and supplemental fluid pump 144, either or both of which may be present. Examples of supplemental fluids are drugs and anticoagulant (e.g., citrate, heparin).

Pressure sensors may be provided at various points throughout the fluid circuit 121. In particular, an arterial pressure sensor 112 may detect pressure of the blood in the blood line 139 upstream of the arterial blood pump 110. In embodiments, each pump contributing to flow balance may have a pressure sensor up stream of it to ensure that pressure compensated control of its speed can be provided. For example, an additional treatment fluid pump pressure sensor 119 may be provided. In embodiments, pressure sensors used for pressure compensated speed control are positioned such that they provide a reliable and consistent indication of pressure upstream of the respective pump or pumps. Thus, they may be positioned close or at least such that there are no intervening possible interferences such as tube lengths that could become kinked. A blood inlet pressure sensor 108 may detect pressure of the blood in the arterial blood line 139 downstream of the arterial blood pump 110 and upstream of the treatment device 114. A blood outlet pressure sensor 106 may detect pressure of the blood in the venous blood line 137 upstream of the venous blood pump 104 and downstream of the treatment device 114. A venous blood pressure sensor 102 may detect pressure in the venous blood line 137 downstream of the venous blood pump 104 and upstream of the patient access 122. The controller 140 receives signals from each of the arterial pressure sensor 112, blood inlet pressure sensor 108, blood outlet pressure sensor 106, and venous blood pressure sensor 102 as well as an air sensor 118 that is positioned to detect air in the fresh treatment fluid line 127. The controller 140 is also connected to control each of the arterial blood pump 110, venous blood pump 104, replacement fluid pump 116, supplemental fluid pump 142, and supplemental fluid pump 144, as well the waste line clamp 130. Note that the waste line clamp 130 could be replaced by any type of valve that selectively halts or permits flow or another pump.

In alternative configurations, instead of treatment fluid pump 128 and waste line clamp 130 being used to halt flow as described below, a waste fluid pump may be provided in the position of waste line clamp 130, which can halt flow by halting rotation. In any of the embodiments, including the present and further embodiments to be described below or described above, any element identified as a line or fluid line (or fluid circuit) could be any type of flow channel including interconnected tubes including pumping tube segments, channels formed in a cartridge (as a pattern of troughs sealed by an overlying welded film), a pattern-welded pair of weldable sheets, a laminated stack of elements that defines flow channels, or any other device that guides the flow of fluid. Any element identified as a pump may be any type of pump or actuator that is volumetric aka, positive displacement type. Such embodiments of lines and fluid lines or fluid circuits may be disposable or otherwise replaceable components that engage pumps, sensors, and actuators of a treatment machine that includes such pumps, sensors, and actuators as identified in the embodiments. Such a machine may be illustrated schematically in the drawings, but not necessarily as a separate component, for example a pump indicated by a single element may include a pump actuator, e.g., a rotor, that works together with a pump tubing segment of a fluid circuit, while both are indicated by a pump symbol schematically in the drawing. Similarly, sensors and clamps are not illustrated separately in all the drawings. Such a machine may be embodied in multiple separate components and may be generally described as having a receiving adapter to allow the connection of a disposable fluid circuit.

The term, receiving adapter, or similar term is an abstraction that may cover all the various mechanisms that permit the operative association between a permanent device and a disposable or replaceable component which together form one of the apparatuses disclosed or claimed. This applies to all the disclosed and claimed embodiments. For example, the drawings described above and below illustrate a system which, when considering that portions are replaceable, indicate the presence of a blood circuit receiving adapter and a medicament (treatment fluid, dialysate, or similar fluid) receiving adapter. The fluid circuits (including blood circuits) may include treatment components as well as portions that engage with sensors and actuators. Again, these comments apply to all embodiments.

Any element identified as a pressure sensor may be a combination of a fluid circuit portion such as a pressure pod or drip chamber and an electronic transducer such as a strain gauge or displacement encoder connected to an element such as a diaphragm that registers pressure. The foregoing elements are well known classes of devices and further elaboration is not needed to permit the skilled reader to develop the details of working embodiments of the described subject matter. Fluids may be supplied from containers such as bags or inline fluid generators such as used in dialysis clinics.

In a treatment operation of blood treatment system 100, arterial blood pump 110 and venous blood pump 104 pump blood or priming fluid in the directions indicated by the respective arrowhead of each pump symbol. They pump at rates controlled by the controller 140 to approximately balance (equivalently, "equalize") the flow of blood in the arterial blood line 139 against the flow of blood in the venous blood line 137 such that a net take-off of fluid (ultrafiltrate) or a net infusion of fluid takes place (which may be called negative ultrafiltrate). The instantaneous rate of ultrafiltrate referring to net loss of fluid by the patient and negative referring to net gain of fluid by the patient) is achieved through control of the total displaced volume by the arterial pump 110 relative to the venous pump 104. The ultrafiltrate may be established by a predetermined ratio of the flow rates of the arterial 110 and venous 104 pumps if the transfer is spread uniformly over the treatment interval or the net ultrafiltrate may be established in a discontinuous manner by varying the ratio of the flow rates of the arterial 110 and venous 104 pumps to achieve a cumulative ultrafiltrate. Thus, ultrafiltrate volume is established by the total volume transported by the venous pump 104 minus the total volume transported by the arterial pump 110 over the course of a treatment. Ultrafiltrate rate may identify the instantaneous difference between the rates of the venous 104 and arterial 110 pumps.

The controller 140 may be programmed to ensure that the net volume of ultrafiltrate or infused fluid meets a prescribed target which may be stored by the controller 140. The pumping speeds required to achieve commanded flow rates may be determined by the controller 140 using data stored by the controller such as look up tables or formulas. A commanded flow rate refers to the operational property (e.g., shaft speed of a peristaltic pump) that is under directly control of the controller which corresponds, more or less accurately, to a flow rate, conditions that may vary from those used to establish a transfer function defining the relationship between the operational property and an actual flow rate produced by it. The conditions may include manufacturing variability such as pumping tube segment and fluid line diameter, material properties of the pumping tube segment, pump lubrication, as well as factors that change due to operation history and storage such as distortions, material creep, etc. The ratio of flow rate to pump speed may be presented by stored look-up table data to indicate target pump speeds by a relationship between pressure difference and flow rate.

Treatment fluid 124 is pumped by fresh treatment fluid pump 128 at a predefined rate stored in the controller 140, which rate may be selected to correspond to the blood flow rate. The replacement fluid 120 may be pumped at a rate controlled by the controller 140 by controlling the commanded rate of replacement fluid pump 116. The supplemental fluid 134 may be pumped at a rate controlled by the controller 140 by controlling the commanded rate of supplemental fluid pump 142. The supplemental fluid 132 may be pumped at a rate controlled by the controller 140 by controlling the commanded rate of supplemental fluid pump 144. Any of the replacement fluid 120, supplemental fluid 134, or supplemental fluid 132 are optional and may or may not be included, along with the respective lines and pumps, in alternative embodiments.

Valves or pinch clamps identified anywhere in the current patent application may be of any type. For example, flexible membranes closed over cartridge-embedded ports, electrically actuated pinch clamps employing linear actuators such as solenoid plungers or stepper motor actuators may be used. The particular type of valve mechanism does not limit the disclosed subject matter. Line 136 is present to indicate that in alternative embodiments, the supplemental fluids may enter the arterial blood line 139 upstream or downstream of the arterial blood pump 110.

The return temperature of blood may be continuously controlled and maintained by the controller 140 in response to a venous return temperature indicated by a venous return temperature sensor 105. Venous return temperature sensor 105 is positioned and configured to detect the temperature of blood in the venous line and output a corresponding signal to the controller.

As indicated above, in any of the embodiments, the fluid balance (net ultrafiltrate volume) resulting from the flows to and from a patient is understood to accrue over a period of time. Thus, although in the embodiments, the controller is described as controlling pumping rates to achieve a fluid balance, optionally offset by a net transfer of fluid to or from the patient (net ultrafiltrate volume), it is understood that the pumping rates need not be constant, define a constant ratio over time, or even define a smoothly varying ratio over time. Since the goal is to control the total loss or gain of fluid from a patient (net ultrafiltrate volume), pumping rates can establish a variety of rates over time such that the cumulative effect is the target ultrafiltrate volume at the end of the treatment. Rates may be constant or vary step-wise, smoothly, and may result in a temporary gain of fluid by the patient during a portion of a treatment interval and net loss during another portion to achieve a total gain or loss for the entire treatment. For another example, the entire fluid gain or loss can be confined to a single part of the treatment interval. The controller may also limit estimated ultrafiltrate so that overall balance does not exceed a certain volume at a given time. A rate of ultrafiltration may also, or alternatively, be limited by the controller.

Figure 2A:
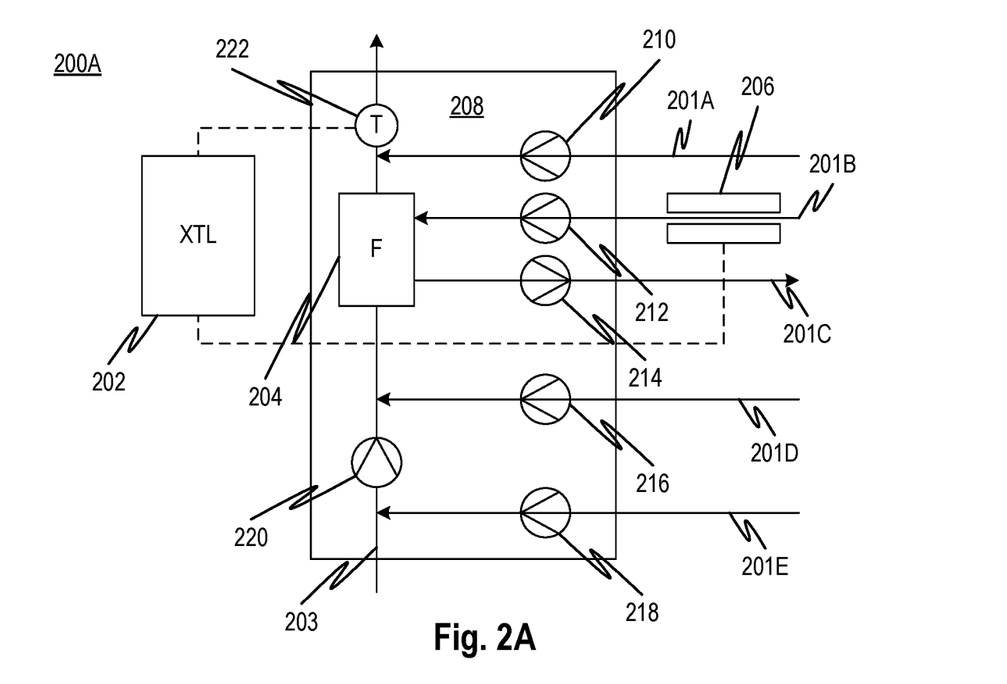
FIG. 2A shows a simplified schematic of a multiple treatment fluid stream system that actively regulates temperatures of at least one stream and includes a controller and treatment device for blood, according to embodiments of the disclosed subject matter.

Referring to FIG. 2A, a blood treatment system 200A has a blood treatment machine 208 engages with a (preferably disposable) fluid circuit that includes a blood line 203 and treatment fluid lines 201A-201E. Blood is pumped by a blood pump 220. For example, the blood pump may be a peristaltic pump. Fluid pumps 210, 212, 214, 216, and 218 engage with treatment fluid lines 201A-201E, respectively to pump treatment fluids in and out of the fluid circuit. Specifically, for example, a treatment fluid conveyed by treatment fluid line 201A may be a post-dilution fluid, drug, or other medicament, which flows directly and is admixed with blood after the blood flows through a treatment device 204 which may also be part of the fluid circuit. Another treatment fluid may flow through treatment fluid line 201B, pumped by fluid pump 212, into the treatment device 204 and out through treatment fluid line 201C, pumped by treatment fluid pump 214. The difference in flow rates of the treatment fluid pump 212 and treatment fluid pump 214 determines a net rate of addition or loss of fluid to or from the pump. Thus, in this embodiment, the fluid balance of the patient will be determined and controlled by regulating the relative speeds of treatment fluid pump 212 and treatment fluid pump 214.

The treatment device 204 transfers heat to or from the treatment fluid circulating through treatment fluid line 201B and treatment fluid line 201C. The treatment fluid line 201B has a temperature regulator 206 to warm or cool, depending on whether the blood is to be heated or cooled.

Another treatment fluid may be conveyed by treatment fluid line 201D may be a pre-dilution fluid, drug, or other medicament, which flows directly and is admixed with blood before the blood flows through the treatment device 204 and after the blood pump 220. The rate of flow through treatment fluid line 201D is regulated by the treatment fluid pump 216. Another treatment fluid may be conveyed by treatment fluid line 201E may be a pre-dilution fluid, drug, or other medicament, which flows directly and is admixed with blood before the blood flows through the treatment device 204 and after the blood pump 220. The rate of flow through treatment fluid line 201E is regulated by the treatment fluid pump 218 whose speed is controlled by the controller 202.

Figure 2B:
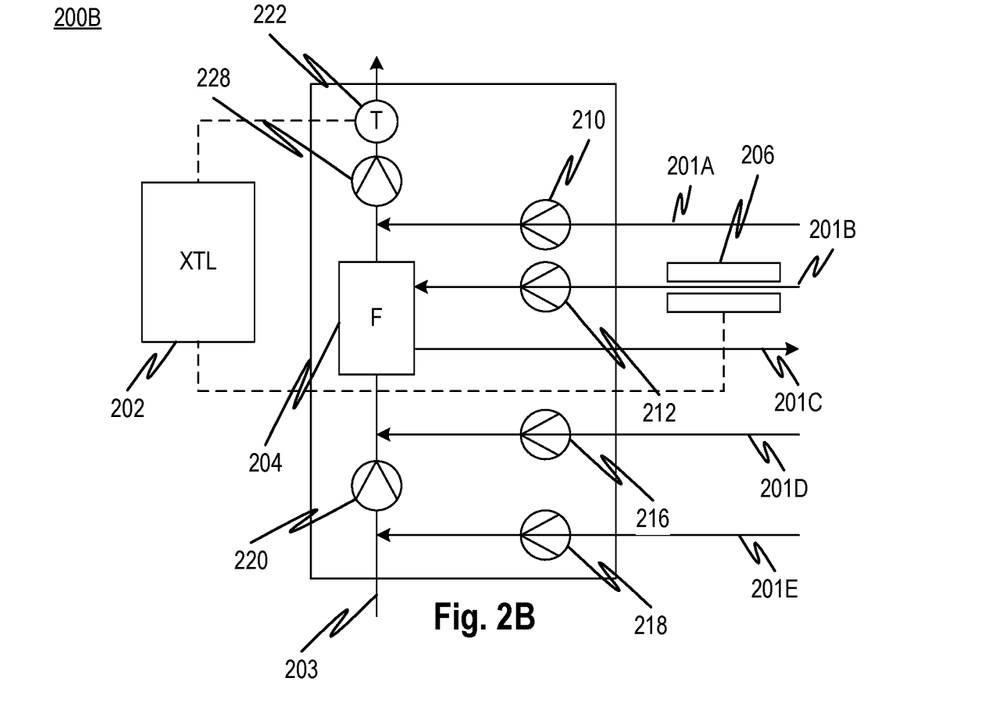
FIG. 2B shows a simplified schematic of a multiple treatment fluid stream system that actively regulates temperatures of at least one stream and includes a controller and treatment device for blood, according to further embodiments of the disclosed subject matter in which fluid balancing is performed in an alternative method and system from that of FIG. 2A.

FIG. 2B shows a simplified schematic of a multiple treatment fluid stream system 200B that actively regulates temperatures of at least one stream and includes a controller and treatment device for blood, according to further embodiments of the disclosed subject matter in which fluid balancing is performed in an alternative method and system from that of FIG. 2A. Referring now to FIG. 2B, the flow balance employs an arterial blood pump 220 and a venous blood pump 228 whose relative pumping speeds determines the rate of ultrafiltration. In the present embodiment, a single treatment fluid pump 212 is used. The control method of FIG. 4 may be used to regulate the power of temperature regulator 206. In other respects the embodiment of FIG. 2B is the same as the embodiment of FIG. 2A so the corresponding description is not repeated.

Figure 3A:
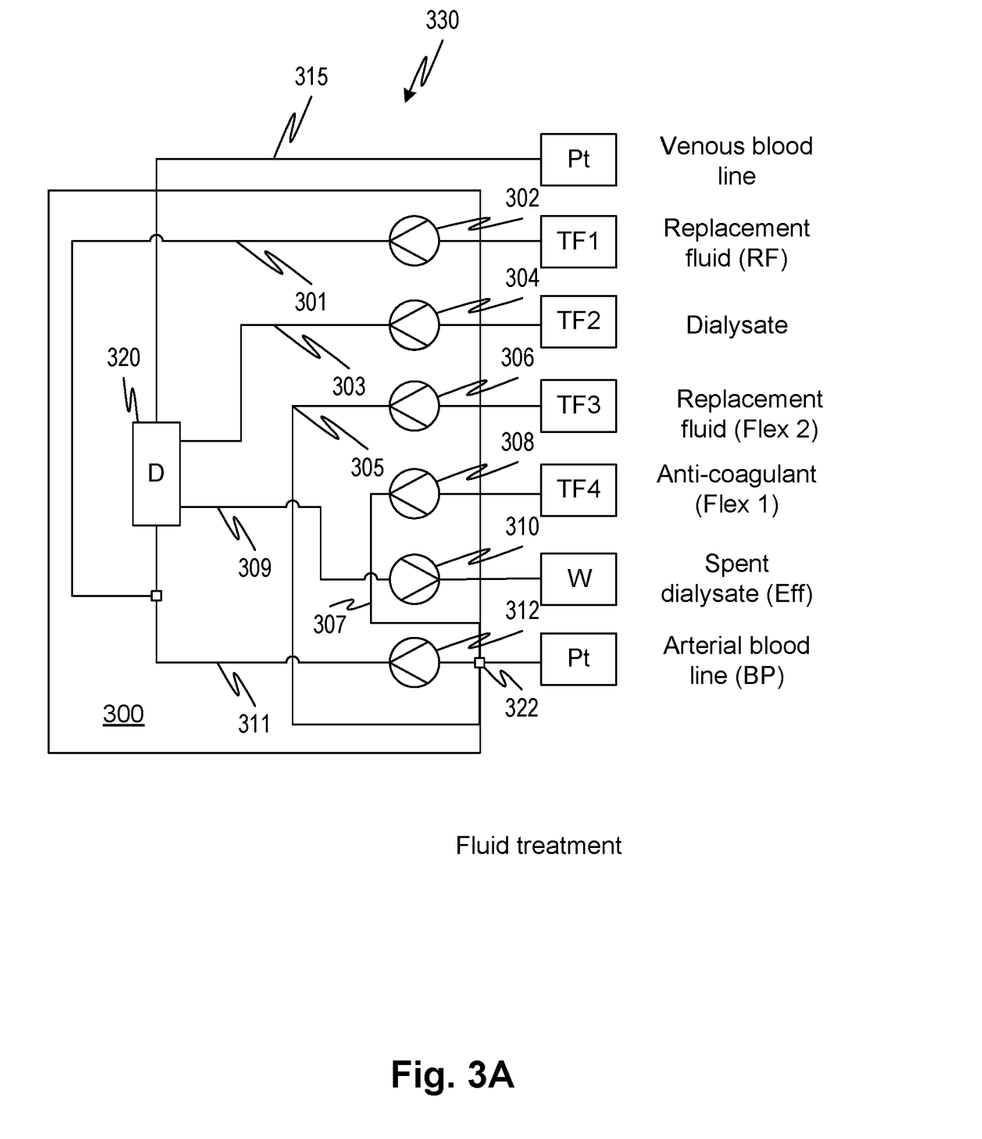
FIG. 3A shows a simplified schematic of a multiple treatment fluid stream system for purposes of discussing how a multiple fluid treatment system can be used, with an alternative fluid circuit, to perform treatments requiring high blood flow, for example blood oxygenation (ECMO).

FIG. 3A shows a simplified schematic of a multiple treatment fluid stream system that includes a multi-stream treatment machine 300 for purposes of discussing how a multiple fluid treatment system can be used, with an alternative fluid circuit, to perform treatments requiring high blood flow, for example blood oxygenation (ECMO). FIG. 3A shows the configuration for pure fluid treatment. A dialyzer 320 receives dialysate through a dialysate line 303 pumped by a dialysate pump 304. Waste dialysate is pumped out of the dialyzer 320 through a waste dialysate line 309 by a balancing pump 310 or some other balancing system. A blood pump 312 pumps blood from a patient through an arterial line 311 into the dialyzer 320. Blood returns to the patient via venous line 315. A pre-dilution replacement fluid is pumped by pump 302 through replacement fluid line 301 into the arterial line 311. Anticoagulant is pumped by a pump 308 through anticoagulant line 307 into arterial line 311. An additional replacement fluid is pumped by pump 306 into arterial line 311 through replacement fluid line 305. Junctions 322 provide inflows from multiple sources. It will be observed that multi-stream treatment machine 300 has multiple pumps (302, 304, 306, 308, 310, and 312). Aside from the blood pump and the waste pump 310 and 312, all the pumps pump fluid into the fluid circuit 330 in such a way that fluids are injected into the dialyzer or directly into the arterial line 311. Also, each of the pumps conveys a different liquid.

Figure 3B:
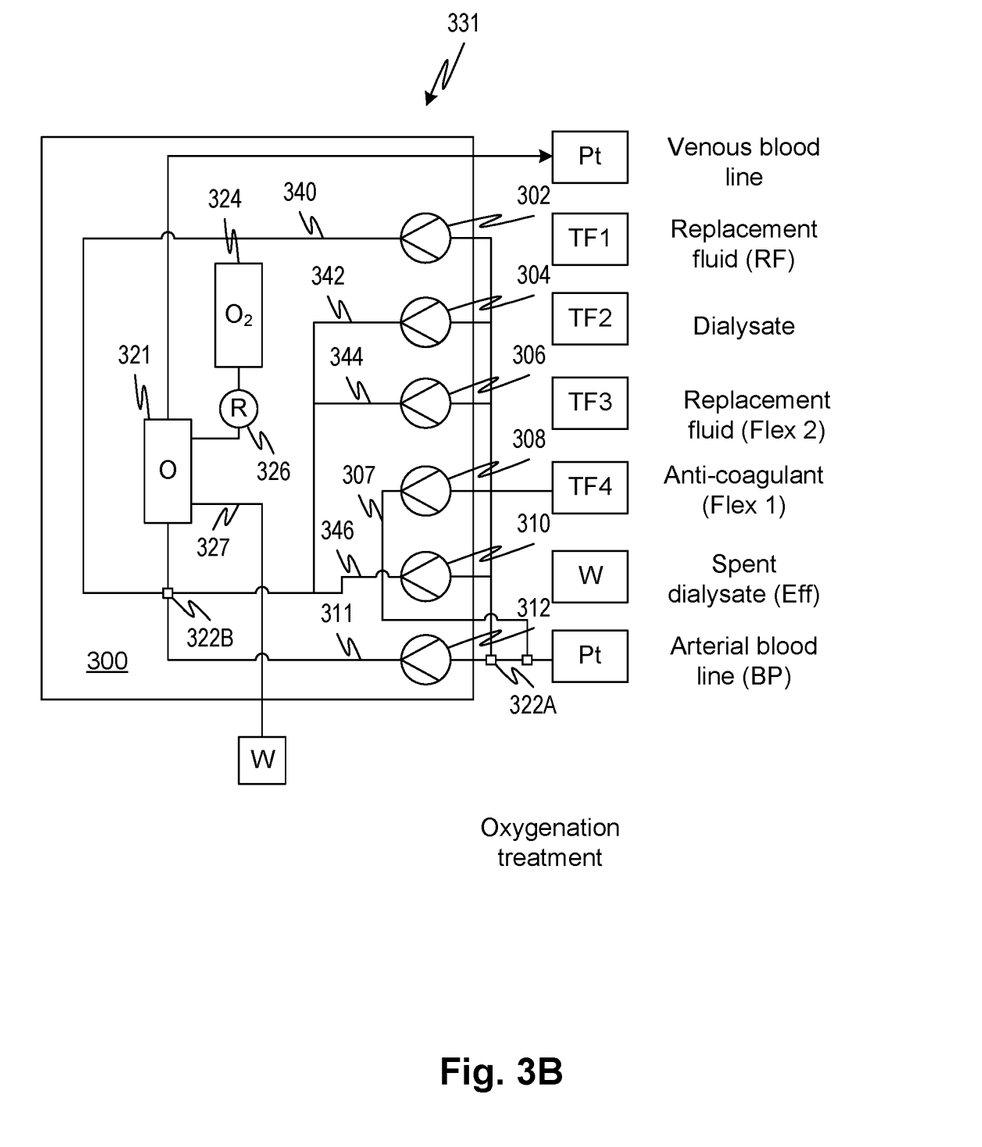
FIG. 3B shows a mode of the same system of FIG. 3A configured with an alternative fluid circuits for high blood flow for ECMO.

FIG. 3B shows a mode of the same system of FIG. 3A configured with an alternative fluid circuits for high blood flow for ECMO. Here, at least two of the pumps are connected by an ECMO blood circuit for parallel blood flow to permit high blood row rates to be obtained with the same pumps as in the multi-stream treatment system. Depending on the number of parallel pumps recruited for blood flow, the rotation rate of one or more pumps may be reversed to provide flow in the desired blood flow direction. In an ECMO treatment circuit 331, multiple lines 340, 342, 344, and 346 are connected in parallel with the arterial line 311. All of these lines diverge from a common junction 322A and converge to a single junction 322B, thereby conveying blood in parallel to an oxygenator 321. The total volume rate of blood is thus equal to the combined volume rates of all the parallel pumps 340, 342, 344, 346, and 311. The oxygenator may be connected to a passive waste line 327 and to a source of oxygen 324 whose pressure is regulated by a regulator 326.

Figure 3C:
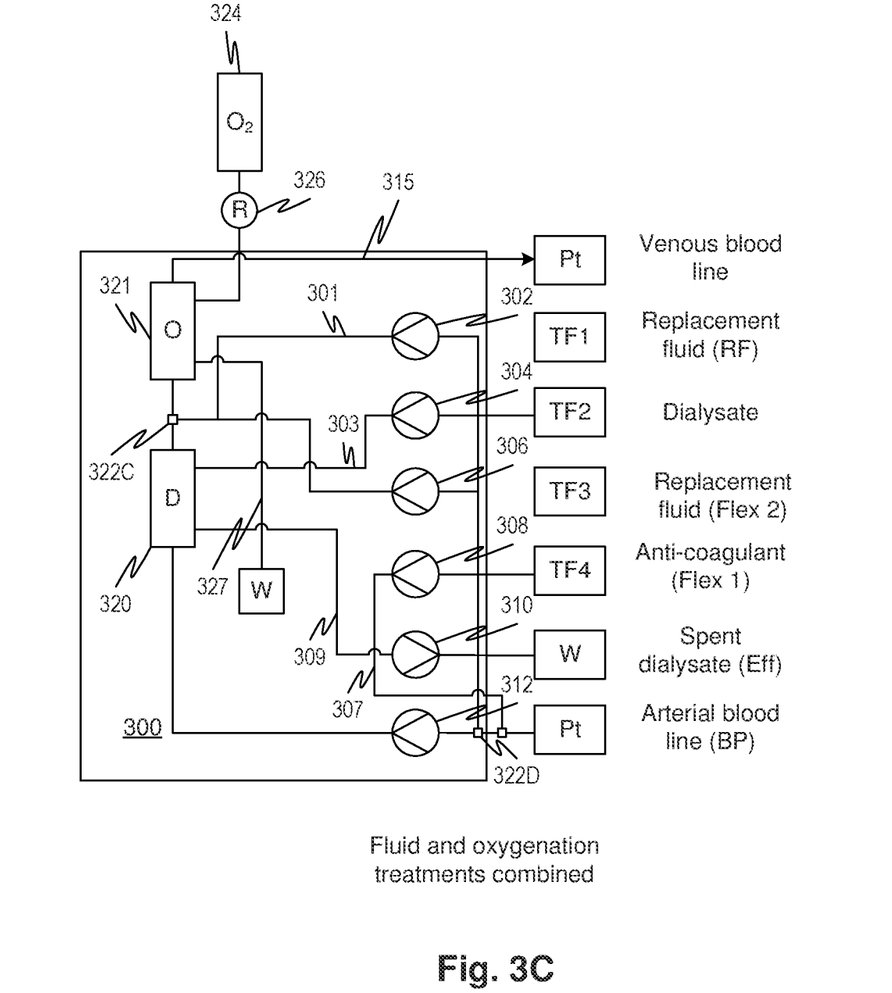
FIG. 3C shows a mode of the same system of FIG. 3A configured with an alternative fluid circuits for high blood flow for ECMO plus fluid treatment, such as dialysis.

FIG. 3C shows a mode of the same system of FIG. 3A configured with an alternative fluid circuits for high blood flow for ECMO plus fluid treatment, such as dialysis. A dialyzer 320 receives dialysate through a dialysate line 303 pumped by a dialysate pump 304. Waste dialysate is pumped by of the dialyzer 320 by a balancing pump 310 or some other balancing system. A blood pump 312 pumps blood from a patient through an arterial line 311 into the dialyzer 320. Blood returns to the patient via venous line 315. Pumps 302 and 306 draw blood from the patient via junction 322D and convey it to a junction 322C where the blood from the dialyzer 320 is also received. Thus three pumps convey blood in parallel to the oxygenator 321 which receives oxygen from the oxygen source 324 regulated by pressure regulator 326. In this way, blood may be dialyzed at a blood flow rate that is suitable for dialysis treatment while oxygenating blood at a rate that is relevant for that purposes. The Note that FIGS. 3A to 3C are less detailed views of a system which may include many details such as those shown in FIGS. 1 and 2A-2B. These details include a controller, pressure sensors, and other sensors. The pumps may be regulating in all such systems according to known principles. For example, the controller may determine the volume rate of flow of blood from the pump rotation rate and the upstream pressure head of the pump. Each pump in any of the above systems may be provided with a pressure sensor, such as a pressure pod, to measure the pressure upstream of the pump. In this way pressure compensation may be used to calculate the flow rate from the pump rotation speed more accurately using a pump calibration curve. In parallel flow this may be very relevant because of differences between the flow lengths upstream of the different flow paths. The controller may use the calculated flow rate to allow an operator to request a specified total flow rate through parallel paths through a user interface. Further details such as the nature of the flow channels, filters, dialyzers, couplings, and the exact nature of the pumps are not specified but the skilled practitioner has not difficulty in applying the described principles to embodiments with a variety of configuration details so their presentation here is not essential to enablement of the inventive subject matter. Peristaltic pumps may be used in embodiments. All pumps may be calibrated by the system in advance of treatment to generate pressure compensation pump curves where flow rate is a function of pump speed and upstream fluid pressure.

According to embodiments, the disclosed subject matter includes an accessory fluid circuit for a multiple-stream blood treatment system having at least two pumps, at least one of which includes a blood pump. The accessory fluid circuit includes a first junction connected to an arterial access connector and a second junction connected to a blood oxygenator connector. At least two parallel pumping tube segments connect the first and second junctions so that parallel pumping tube segments are fluidically connected for parallel flow between the arterial connector and the blood oxygenator connector.

In variations, the fluid circuit may be provided with instructions for using the multiple-stream blood treatment system including an instruction to operate a pump in a reverse direction relative to a normal mode.

In further variations, including other identified variations, the at least two pumps include a blood pump and a replacement fluid pump. In still further which may be combined with other identified variations, the multiple-stream blood treatment system is configurable for delivering a hemodialysis treatment.

According to embodiments, the disclosed subject matter includes a method of performing blood treatments. The method includes, at a first time, connecting a first fluid circuit to, and performing a first blood treatment by operating, a machine with at least two pumps. The method includes, at a second time, connecting a second fluid circuit to, and performing a blood oxygenation treatment by pumping blood in parallel using the at least two pumps, thereby to obtain a higher blood flow rate than a maximum rate of either of the at least two pumps alone. The method includes, at the second time, applying blood from the at least two pumps to a blood oxygenator.

In variations, of the method, the first blood treatment is a hemodialysis or hemofiltration treatment that includes the dilution of blood with a medicament. In further variations of the method, the first blood treatment is a hemodialysis or hemofiltration treatment that includes the dilution of blood with a replacement fluid. In still further variations, which may include the other identified variations, the first blood treatment is a hemodialysis or hemofiltration treatment that includes the dilution of blood with an anticoagulant medicament.

According to embodiments, the disclosed subject matter includes a method of performing a high blood flow treatment. The method includes using a low blood flow extracorporeal blood treatment device having pumps used for replacement fluid or anticoagulant, installing a blood circuit that routes blood to at least two of the pumps in parallel. The method further includes pumping the blood with said pumps, combining two resulting blood flows into a single high flow treatment device; and returning treated blood at a high flow rate to a patient.

In variations of the method, the high blood flow rate is higher than a rated capacity of the extracorporeal blood treatment device. In further variations, which may include the other identified variations, the blood treatment device includes an oxygenator.

According to embodiments, the disclosed subject matter includes an apparatus for controlling flow in a fluid circuit. A treatment machine has pumps and a controller connected to control the flow of the pumps that respectively convey blood and at least another fluid through a first predefined fluid circuit. A high blood flow fluid circuit, with two parallel flow paths each having a pumping tube segment, is attachable to at least two of the pumps so that they pump blood in in parallel to increase the flow of blood as compared to when one of the pumps is used to pump the other fluid.

In variations of the apparatus, the treatment machine is a dialysis machine. In further variations, which may include other identified variations thereof, the high flow fluid circuit includes a blood oxygenator. In still further variations, which may include other identified variations, the high flow fluid circuit includes a blood oxygenator. In still further variations, which may include the other identified variations, the controller includes a programmable controller that has been programmed to implement a method whereby it computes the total flow through the parallel flow paths responsively to upstream pressure measurements at each of the at least two of the pumps.

Figure 4:
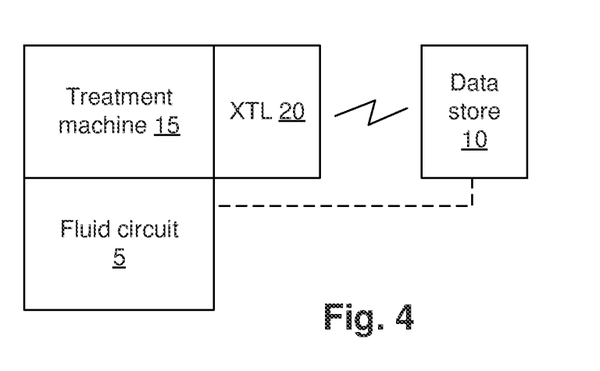
FIG. 4 is a figurative illustration of a treatment machine and an attached fluid circuit for discussion of automatic determination of the type of fluid circuit so that, for example, the treatment machine can switch from a normal treatment mode to one requiring high blood flow according to the type of fluid circuit attached to it.

FIG. 4 is a figurative illustration of a treatment machine and an attached fluid circuit for discussion of automatic determination of the type of fluid circuit so that, for example, the treatment machine can switch from a normal treatment mode to one requiring high blood flow according to the type of fluid circuit attached to it. The configuration that allows the treatment machine 15 controller 20 to read from a data store 10 the type of fluid circuit being attached and to program the controller accordingly. In embodiments, the controller 20 reads the data in the data store 10, for example bar code or RFID, and operates the pumps appropriately for the type of fluid circuit being attached. So in this way the treatment machine 15 may determine the number of pumps, the directions of flow, the speeds, and any other suitable information required to provide a treatment that is consistent with the attached type of fluid circuit. Thus, by connecting the fluid circuit 5 to the treatment machine 15, the controller 20 reads the data store 10 and programs itself for the correct treatment corresponding to the attached fluid circuit 5 type.

It will be appreciated that the modules, controllers, processes, systems, and sections described above can be implemented in hardware, hardware programmed by software, software instruction stored on a non-transitory computer readable medium or a combination of the above. For example, a method for performing multiple treatment modes, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java™ class-based, object-oriented programming language, C++, C#.net or the like. The instructions can also comprise code and data objects provided in accordance with, for example, the Visual Basic™ language, LabVIEW™ graphical programming language, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of controllers and especially digital controllers and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, blood treatment methods and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

The invention claimed is:

1. A multiple treatment fluid stream system, comprising:
a multi-stream treatment machine including at least two pumps, at least one of which is a blood pump and at least one other of which is a multiple-fluid pump that pumps one of replacement fluid, dialysate, anti-coagulant, and spent dialysate in an extracorporeal blood treatment mode and pumps blood in an extracorporeal membrane oxygenation mode; and
an accessory fluid circuit comprising:
a first junction connected to an arterial access connector;
a second junction connected to a blood oxygenator connector; and
at least two parallel pumping tube segments including a first pumping tube segment and a second pumping tube segment, the first pumping tube segment connected to the first junction and also connected to the second junction, the second pumping tube segment connected to the first junction and also connected to the second junction, wherein the first pumping tube segment and the second pumping tube segment provide parallel flow paths for the blood from the arterial access connector to the blood oxygenator connector,
the blood that enters the accessory fluid circuit from the arterial access connector splits into a first blood stream that flows through the first pumping tube segment and a second blood stream that flows through the second pumping tube segment, and
the first blood stream and the second blood stream combine into a combined blood stream at the second junction.

2. The multiple treatment fluid stream system as in claim 1, further comprising instructions for using the multiple treatment fluid stream system including an instruction to operate the multiple-fluid pump in a reverse direction relative to the extracorporeal blood treatment mode.

3. The multiple treatment fluid stream system as in claim 1, wherein the multiple-fluid pump is a replacement fluid pump.

4. The multiple treatment fluid stream system as in claim 1, wherein the multiple treatment fluid stream system is configurable for delivering a hemodialysis treatment.

5. The multiple treatment fluid stream system as in claim 1, wherein
the second junction is upstream of the blood oxygenator connector, and
the combined blood stream is supplied to the blood oxygenator connector.

6. A method of performing blood treatments, comprising:
at a first time, connecting a first fluid circuit to, and performing a first blood treatment by operating a machine that includes at least two pumps, a first pump of the at least two pumps conveying blood through a first pumping tube segment of the first fluid circuit, a second pump of the at least two pumps conveying a fluid that includes one of replacement fluid, dialysate, anti-coagulant, and spent dialysate through a second pumping tube segment of the first fluid circuit;
at a second time, connecting a second fluid circuit that has a different configuration from the first fluid circuit, to the machine, and performing a blood oxygenation treatment by the machine using the second fluid circuit, wherein
the blood oxygenation treatment includes pumping the blood from an arterial access connector in parallel flow paths using the at least two pumps to a blood oxygenator, the first pump conveying a first portion of the blood through a first pumping tube segment of the second fluid circuit, the first pumping tube segment of the second fluid circuit connected to a first junction and also connected to a second junction, the second pump conveying a second portion of the blood through a second pumping tube segment of the second fluid circuit, the second pumping tube segment of the second fluid circuit connected to the first junction and also connected to the second junction, and
wherein the blood that enters the second fluid circuit from the arterial access connector splits at the first junction into the first portion of the blood that flows through the first pumping tube segment of the second fluid circuit and the second portion of the blood that flows through the second pumping tube segment of the second fluid circuit, and
the first portion of the blood and the second portion of the blood combine into a combined blood stream at the second junction.

7. The method of claim 6, wherein the first blood treatment is a hemodialysis or hemofiltration treatment that includes dilution of the blood with a medicament.

8. The method of claim 6, wherein the first blood treatment is a hemodialysis or hemofiltration treatment that includes dilution of the blood with a replacement fluid.

9. The method of claim 6, wherein the first blood treatment is a hemodialysis or hemofiltration treatment that includes dilution of the blood with an anti-coagulant.

10. The method of claim 6, wherein
the second junction is upstream of the blood oxygenator, and the combined blood stream is supplied to the blood oxygenator.

\* \* \* \* \*